US012753139B2

(12) United States Patent
Hasenstab-Riedel et al.

(10) Patent No.: US 12,753,139 B2
(45) Date of Patent: Oct. 6, 2026

(54) CATALYTIC METHOD FOR THE PREPARATION OF PERFLUOROALKOXY-SUBSTITUTED ARENES AND HETEROARENES

(71) Applicant: Freie Universität Berlin, Berlin (DE)

(72) Inventors: Sebastian Hasenstab-Riedel, Kleinmacknow (DE); Matthew Hopkinson, Berlin (DE); Stefan Dix, Berlin (DE); Paul Golz, Frankfurt (DE); Jonas Rachid Schmid, Berlin (DE); Holger Pernice, Schwanewede (DE); Sebastian Gutmann, Hannover (DE)

(73) Assignee: FREIE UNIVERSITÄT BERLIN, Berlin (DE)

( * ) Notice: Subject to any disclaimer, the term of this patent is extended or adjusted under 35 U.S.C. 154(b) by 541 days.

(21) Appl. No.: 18/547,486

(22) PCT Filed: Feb. 21, 2022

(86) PCT No.: PCT/EP2022/054181

§ 371 (c)(1),
(2) Date: Aug. 22, 2023

(87) PCT Pub. No.: WO2022/175508

PCT Pub. Date: Aug. 25, 2022

(65) Prior Publication Data

US 2024/0150271 A1 May 9, 2024

(30) Foreign Application Priority Data

Feb. 22, 2021 (EP) .................................... 21158495

(51) Int. Cl.
*C07C 41/06* (2006.01)
*B01J 31/02* (2006.01)

(52) U.S. Cl.
CPC ........... *C07C 41/06* (2013.01); *B01J 31/0235* (2013.01); *B01J 31/0248* (2013.01); *B01J 2531/16* (2013.01); *B01J 2531/821* (2013.01); *B01J 2531/827* (2013.01); *B01J 2540/50* (2013.01)

(58) Field of Classification Search
CPC ...................................................... C07C 41/06
See application file for complete search history.

(56) References Cited

U.S. PATENT DOCUMENTS 4,077,857 A * 3/1978 Toy ........................ B01J 19/123
204/157.92
2021/0032181 A1 2/2021 Ngai et al.

FOREIGN PATENT DOCUMENTS

| | | | |
|---|---|---|---|
| EP | 1757581 | A1 | 2/2007 |
| WO | 2011044181 | A1 | 4/2011 |
| WO | 2014096414 | A1 | 6/2014 |
| WO | 2019207020 | A1 | 10/2019 |

OTHER PUBLICATIONS

W. J. Peláez, et al., 51(40), Tetrahedron Letters, 5242-5245(2010) ("Peláez") (Year: 2010).*
J. W. Lee, et al. 132.48 Angewandte Chemie 21659-21664 (2020)("Lee") (Year: 2020).*
A. Tlili et.al, "Synthetic Approaches to Trifluoromethoxy-Substituted Compounds" Angew Chem Int Ed., 2016, 55 (39), 11726-11735 (10 pages).
B. Manteau et. al., "A General Approach to (Trifluoromethoxy) Pyridines: First X-ray Structure Determinations and Quantum Chemistry Studies" Er. J. Org. Chem., 2010, vol. 2010, Issue 31, 6043-6066 (25 pages).
M. S. Toy et. al., "Photochemical Reactions of Perfluorodialkyl Peroxides with Perfluorocycloolefins" Journal of Fluorine Chemistry, 1976, vol. 7, Issue 4, pp. 375-383 (9 pages).
E.F.Witucki, "Addition of Fluoroperoxides to Perfluorovinylsulfur Pentafluoride" Journal of Fluorine Chemistry, 1982, vol. 20, pp. 807-811 (5 pages).
W.J.Pelaez, "Cothermolysis: A One Pot Synthetic Method for Novel 2-substituted 5-(Trifluoromethoxy) Thiophenes" Tetrahedron Letters, 2010, vol. 51, pp. 5242-5245 (4 pages).
J. Jelier et al., "Radical Trifluoromethoxylation of Arenes Triggered by a Visible Light Mediated N—O Bond Redox Fragmentation" Angew Chem Int. Ed., 2018, vol. 57, pp. 13784-13789 (6 pages).
D Hanss, J.C. Freys, G.Bernandinelli, "Cyclometalated Iridium(III) Complexes as Photosensitizers for Long-Range Electron Transfer: Occurrence of a Coulomb Barrier" European Journal of Inorganic Chemistry, 2009, vol. 2009, Issue 32, pp. 4850-4859 (11 pages).
Zheng Weijia et al., "Redox Active Reagents for Photocatalytic Generation of the OCF 3 Radical and (Hetero) Aryl C-H Trifluoromethoxylation" Angewandte Chemie International Edition, vol. 57, No. 42, Sep. 20, 2018, pp. 13795-13799 (5 pages).
Zheng Weijia et al., "Catalytic C—H Trifluoromethoxylation of Arenes and Heteroarenes" Angewandte Chemie International Edition, vol. 57, No. 31, 2018, pp. 9645-9649 (5 pages).

(Continued)

*Primary Examiner* — Alexander R Pagano
*Assistant Examiner* — Frank S. Hou
(74) *Attorney, Agent, or Firm* — Osha Bergman Watanabe & Burton LLP

(57) ABSTRACT

The present invention is directed to methods for the preparation of $(C_nF_{2n+1})$O-substituted arenes and heteroarenes and the direct perfluoroalkylation of arenes and heteroarenes with a $(C_nF_{2n+1})$O-group, respectively, characterized in that a peroxide reagent according to the general formula (I): $(C_nF_{2n+1})2$ (I) is fragmented in the presence of an electron transferring catalyst under $(C_nF_{2n+1})$O-radical formation, and said $(C_nF_{2n+1})$O-radical then substitutes a C—H bond of an arene or heteroarene C—H bond with a $(C_nF_{2n+1})$O-group, wherein in the above formulae, n is an integer in the range from 1 to 4.

20 Claims, 2 Drawing Sheets

(56) References Cited

OTHER PUBLICATIONS

Dix Stefan et al., "Radical C—H Trifluoromethoxylation of (Hetero) arenes with Bis(trifluoromethyl) Peroxide" Chemistry—A European Journal, vol. 27, No. 45, 2021, pp. 11554-11558 (6 pages).

International Search Report issued in International application No. PCT/EP2022/054181 dated Jun. 8, 2022 (5 pages).

Written Opinion issued in International application No. PCT/EP2022/054181 dated Jun. 8, 2022 (9 pages).

Office Action issued in Chinese Application No. 202280015576.8, mailed on Jul. 8, 2025 (14 pages).

* cited by examiner a)

Celikalim

NMS-P937

Riluzole b)

Thifluzamide

Flucarbazone-sodium c)

Toronto Research Chemicals US$120,000/g

Matrix Scientific US$15,680/g

Sigma Aldrich US$10,000/g

Sigma Aldrich US$10,000/g

CATALYTIC METHOD FOR THE PREPARATION OF PERFLUOROALKOXY-SUBSTITUTED ARENES AND HETEROARENES

This application claims priority to International Application No. PCT/EP2022/054181 filed on Feb. 21, 2022, which claims priority to European Application No. 21158495.8 filed on Feb. 22, 2021, the entire contents of which are hereby incorporated by reference for all purposes.

TECHNICAL FIELD

The present invention relates to methods for the direct C—H perfluoroalkoxylation of arenes and heteroarenes.

BACKGROUND

Fluorinated organic compounds often have interesting pharmacological properties. The introduction of fluorine atoms and fluorinated organic groups therefore plays an important role in the development of pharmaceutical and agrochemical targets as well as for the provision of building blocks useful in the synthesis of such compounds.

Among the fluorine containing functional groups, perfluoroalkoxy groups, in particular the trifluoromethoxy ($OCF_3$) group, is of great interest because of unique structural and electronic properties which can be useful not only in pharmaceutical, but also in materials and agricultural sciences. Examples of important $OCF_3$-substituted a) pharmaceuticals, b) agrochemicals and c) building blocks known in the art are shown in FIG. 1.

Yet, the introduction of perfluoroalkoxy groups into organic molecules is challenging. There are only very limited possibilities for the synthesis of perfluoroalkoxy-substituted molecules. Methods often suffer from poor substrate scope and/or require a multi-step sequence in order to finally arrive at the perfluoroalkoxy-substituted target compound.

Known approaches for the introduction of perfluoroalkoxy groups into organic molecules include the de novo construction of the perfluoroalkoxy group in the molecule; the indirect perfluoroalkylation of aliphatic and (hetero) aromatic alcohols by means of reaction with an electrophilic perfluoroalkyl donor; and the direct perfluoroalkoxylation of organic molecules using a perfluoroalkoxy donor reagent (for a minireview on "Synthetic approaches to Trifluoromethoxy-Substituted Compounds", see: A. Tlili et al., Angew. Chem. Int. Ed. 2016, 55, 11726-11735). Limitations for the de novo construction of trifluoromethoxylated pyridines are that hydroxypyridines are used as substrates and that the final halogen exchange step is performed with stoichiometric $SbF_3$. Most importantly, this method can only be applied on ortho-chloro pyridines (B. Manteau et al. "A General Approach to (Trifluoromethoxy)pyridines: First X-ray Structure Determinations and Quantum Chemistry Studies", Eur. J. Org. Chem. 2010, 6043-6066). Any other functionality, such as nitrile or amine functionalities, therefore has to be introduced in a multi-step procedure that often includes expensive palladium catalyzed reactions.

Bis-perfluoroalkylperoxides, such as e.g. bis-trifluoromethylperoxide ($CF_3OOCF_3$ or $(OCF_3)_2$) and bis-perfluoro-tert-butylperoxide ($((CF_3)_3COOC(CF_3)_3$ or $(OC(CF_3)_3)_2$), have been used as perfluoroalkoxy donor reagents in a photochemical reaction with perfluorocycloolefins (M. S. Toy et al, Journal of Fluorine Chemistry, 7 (1976) 375-383). In that case, a strong ultra-violet source was required for the homolytic fragmentation of the peroxide in order to form the perfluoroalkoxy radical which then added to the olefin bond of the perfluorocycloolefin substrate.

Bis-trifluoromethylperoxide has also been used as a donor reagent for the addition of $OCF_3$ to the substrate $CF{=}CFSF_5$, where the $CF_3O$ radical was generated either thermally by heating the reactants at 185° C. for 15 hrs, or by UV-photolysis by irradiating the reactants for one day at ambient temperature (E. F. Witucki, "Addition of Fluoroperoxides to Perfluorovinylsulfur Pentafluoride", Journal Fluorine Chemistry 20 (1982) 807-811).

Bis-trifluoromethylperoxide has furthermore been used for the trifluoromethoxylation of 2-substituted thiophenes (W. J. Piláes, "Co-thermolysis: a one-pot synthetic method for novel 2-substituted 5-(trifluoromethoxy)thiophenes", Tetrahedron Letters 51 (2010) 5242-5245). However, this reaction also requires relatively harsh conditions as it is carried out at 200° C. in the gas phase.

Due to the harsh conditions required and the poor substrate scope in the direct perfluoroalkoxylation of organic molecules with bis-perfluoroalkylperoxides, such as bis-trifluoromethylperoxide $(OCF_3)_2$, these reagents are commonly considered as having limited utility in the perfluoroalkoxylation of organic molecules including arenes and heteroarenes. Probably in view of this situation, the company Air Products and Chemicals, Inc., which has a patent on the preparation of high purity fluorinated peroxides including bis-trifluoromethylperoxide (EP 1 757 581), has discontinued the commercial distribution of bis-trifluoromethylperoxide (J. Jelier et al., "Radical Trifluoromethoxylation of Arenes Triggered by a Visible-Light-Mediated N—O Bond Redox Fragmentation", Angew. Chem. Int. Ed. 2018, 57, 13784-13789, reference [13]).

Alternative approaches for the direct introduction of the $OCF_3$ group have been developed. For example, in the above-mentioned publication of J. Jelier et al., a trifluoromethoxy transfer reagent derived from the trifluoromethylation of pyridine N-oxides is used for the catalytic trifluoromethylation of arenes triggered by light-mediated N—O bond redox fragmentation. However, the preparation of the trifluoromethoxy transfer reagent used in J. Jelier et al. involves the "Togni Reagent I" (3,3-Dimethyl-1-(trifluoromethyl)-1,2-benziodoxol), which is relatively expensive. Accordingly, trifluoromethoxy transfer reagents that need to be produced with "Togni Reagent I" are less attractive for industrial applications. Similar considerations apply to trifluoromethoxy transfer reagents prepared from Togni Reagent II (1-(Trifluoromethyl)-1,2-benzoiodoxol-1(1H)-on.

Hence, if methods benefiting from an enhanced practicability of bis-perfluoroalkylperoxides as perfluoroalkoxy donors were available, these would serve as valuable tools for the direct perfluoroalkoxylation of organic molecules. It would also be desirable if such methods allowed access to a variety of perfluoroalkoxylated substrates, including perfluoroalkoxylated arenes and heteroarenes.

SUMMARY OF THE PRESENT INVENTION

The present invention addresses these needs by the provision of methods according to the following items:

[1] Method for the preparation of $(C_nF_{2n+1})O$-substituted arenes and heteroarenes characterized in that a peroxide reagent according to the following general formula (I)

$$(OC_nF_{2n+1})_2 \qquad (I)$$

is fragmented in the presence of an electron transferring catalyst under $(C_nF_{2n+1})O$-radical formation, and said $(C_nF_{2n+1})O$-radical then substitutes a C—H bond of an arene or heteroarene with a $(C_nF_{2n+1})O$-group, wherein in the above formulae n is an integer in the range from 1 to 4.

[2] Method for the direct perfluoroalkoxylation of arenes and heteroarenes with a $(C_nF_{2n+1})O$-group, characterized in that a peroxide reagent according to the following general formula (I)

$$(OC_nF_{2n+1})_2 \quad (I)$$

is fragmented in the presence of an electron transferring catalyst under $(C_nF_{2n+1})O$-radical formation, and said $(C_nF_{2n+1})O$-radical then substitutes a C—H bond of an arene or heteroarene with a $(C_nF_{2n+1})O$-group, wherein in the above formulae n is an integer in the range from 1 to 4.

The invention further concerns methods for the preparation of pharmaceutical or agrochemical compounds or building blocks for the synthesis of pharmaceutical and agrochemical compounds, comprising the methods described above.

DETAILED DESCRIPTION OF THE PRESENT INVENTION

In the context of the present invention, the singular form is intended also to include the plural, for example, the term "catalyst" includes mixtures of two or more catalysts. All aspects and embodiments of the present invention are combinable. In the context of the present invention, the term "comprising" is intended to include the meaning of "consisting of" and "consisting essentially of". Endpoints of ranges are also included in the disclosure, e.g. a temperature range of 20° C. to 30° C. includes the values 20° C. and 30° C.

Figure 1:
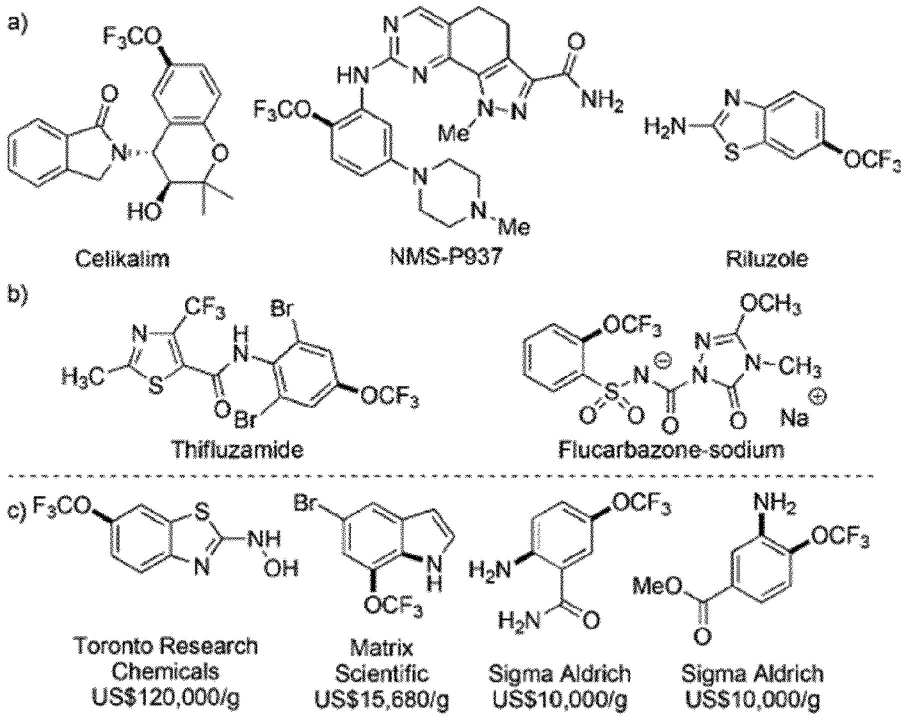
FIG. 1 shows examples of important $OCF_3$-substituted a) pharmaceuticals, b) agrochemicals and c) building blocks known in the art.
Figure 2:
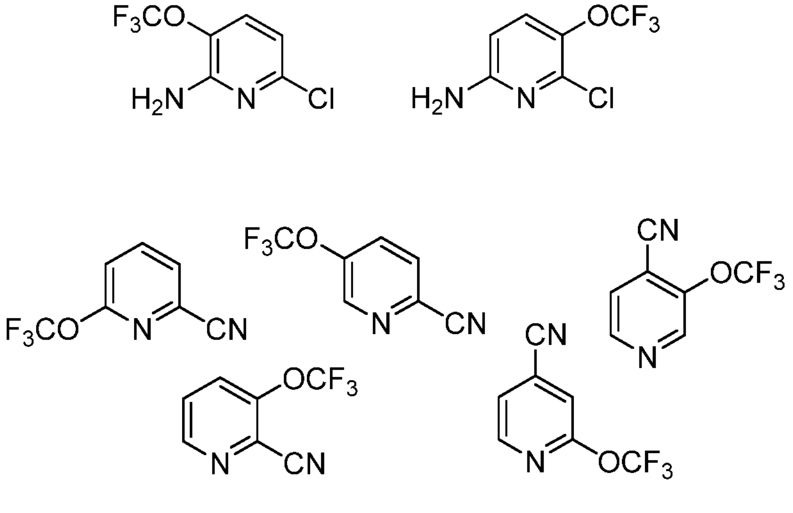
FIG. 2 shows examples of trifluoromethoxy-substituted pyridines in accordance with one or more embodiments.

The present invention uses a catalytic approach for the direct perfluoroalkoxylation of arenes and heteroarenes, and the preparation of $(C_nF_{2n+1})O$-substituted arenes and heteroarenes, respectively (wherein in this formula, n is an integer in the range from 1 to 4). The methods of the present invention allow access to versatile perfluoroalkoxylated arenes and heteroarenes, which may be useful as building blocks in the synthesis of pharmaceutical and agrochemical target compounds, in one step. Such building blocks of commercial interest e.g. include trifluoromethoxy-substituted pyridines as shown in FIG. 2, which are amino-, halo- and/or cyano-substituted pyridines. The building blocks shown in FIG. 2 are directly accessible in one step from the corresponding non-trifluoromethoxylated pyridines following the methods of the present invention, and can be used for further functionalization, e.g. for amide formation (from the amino group), for ipso-substitution of the chloro group, for cyclization of the nitrile group, and for hydrolyzation of the nitrile group into a carboxyl-group (which, again, can be used for further functionalization, e.g. amide formation).

WO 2011/044181 A1, for example, discloses in Scheme 25 (step 1) and 26 (step 1-4) the preparation of 5-trifluoromethoxy picolinic acid, which is further transferred into a pharmaceutically active compound (designated as Example 123 in WO 2011/044181 A1). 5-trifluoromethoxy picolinic acid is prepared from 2-cyano-5-trifluoromethoxy pyridine, which can be obtained in one step from 2-cyanopyridine following the methods of the present invention. In WO 2011/044181 A1, a four step sequence starting from 2-chloro-5-hydroxy pyridine is required for the preparation of 2-cyano-5-trifluoromethoxy pyridine. Following the methods of the present invention, only one step is required, and hence less reactants, solvents etc. for the preparation of the same compound. Therefore, the methods of the present invention provide economic and ecological advantages over the reaction sequence applied in WO 2011/044181 A1 for the preparation of 2-cyano-5-trifluoromethoxy pyridine.

For carrying out the methods of the present invention, typically a mixture of (hetero)arene, catalyst and, optionally, an additive is provided, optionally in a solvent. Generally, this mixture is cooled (typically using liquid nitrogen) and the peroxide reagent according to the general formula (I) is added to the reaction mixture. The mixing of the reagents at this low temperature can be advantageous for practical reasons, as some of the reagents, such as $(OCF_3)_2$, are gaseous under ambient condition. Often, after the addition of the peroxide reagent, the reaction mixture is allowed to warm up to room temperature (which for the purpose of the present invention is defined as a temperature between 20 and 30° C.) and allowed to stir until the conversion is complete. Advantageously, the reaction is carried out under protective gas, such as e.g. nitrogen or argon. The foregoing is not intended to limit the methods; other sequences of addition of reactants, solvents, catalyst and additives as well as temperatures are also feasible. The methods can be carried out batch-wise or in a continuous procedure.

The perfluoroalkoxylated arenes and heteroarenes resulting from the methods of the present invention in some instances are obtained as a mixture of regioisomers (of course only in those cases where the formation of regioisomers is possible). For the purification of the reaction mixture and the isolation of the perfluoroalkoxylated products, purification techniques known to the skilled person, such as chromatographic methods (e.g. column chromatography on a laboratory scale or HPLC) and distillation methods (including distillations on an industrial scale), can be feasibly used.

"Direct perfluoroalkoxylation" in the context of the present invention is defined in accordance with the common understanding of the skilled person, namely that the $(C_nF_{2n+1})O$-group is introduced by means of a $(C_nF_{2n+1})O$-donor reagent (wherein in these formulae, n is an integer in the range from 1 to 4). In the present case, the donor reagent is the peroxide reagent according to the general formula (I): $(OC_nF_{2n+1})_2$ (I), wherein n is an integer in the range from 1 to 4. The methods of the present invention improve the usefulness of bis-perfluoroalkylperoxides according to the general formula (I) as a reagent for the direct perfluoroalkoxylation of arenes and heteroarenes, and allow the preparation of $(C_nF_{2n+1})O$-substituted arenes and heteroarenes in one step (wherein in this formula, n is an integer in the range from 1 to 4).

The peroxide reagents suitable for use in the present invention include $(OCF_3)_2$, $(OC_2F_5)_2$, $(O\text{-n-}C_3F_7)_2$, $(O\text{-iso-}C_3F_7)_2$, $(O\text{-n-}C_4F_9)_2$, $(O\text{-iso-}C_4F_9)_2$ and $(O\text{-tert-}C_4F_9)_2$, thus reflecting all integers 1, 2, 3 and 4=n, wherein $(OCF_3)_2$ and $(O\text{-tert-}C_4F_9)_2$ are preferred peroxide reagents for use in the present invention. The skilled person is familiar with methods for the preparation of these peroxide reagents. A method for the preparation of $(OCF_3)_2$ is e.g. disclosed in EP 1 757 581.

The methods of the present invention hence allow access to $CF_3O$—, $C_2F_5O$—, n-$C_3F_7O$—, iso-$C_3F_7O$, n-$C_4F_9O$—, iso-$C_4F_9O$, tert-$C_4F_9O$-substituted arenes and heteroarenes, with $CF_3O$- and tert-$C_4F_9O$-substituted arenes and heteroarenes being preferred target compounds.

The methods according to the present invention are catalytic methods which use an "electron transferring catalyst" for the C—H substitution of arenes and heteroarenes with a perfluoroalkoxy-group derived from the peroxide reagent according to the general formula (I).

"Electron transfer" in accordance with the common understanding of the skilled person means the relocation of an electron from a chemical entity being an atom, ion or molecule to another such chemical entity, which results in a change of oxidation state of the chemical entities involved. Electron transfer can also occur between an electrode and a chemical entity.

A "catalyst" for the purpose of the present invention is defined in accordance with the common understanding of the skilled person in the art, i.e. it is a substance, which increases the rate of a chemical reaction by lowering the activation barrier. The catalyst is not consumed by means of the catalyzed reaction but can act repeatedly in said reaction. In the present invention, this means that the method is carried out preferably with substoichiometric amounts of the catalyst, however, it is also possible to carry out the methods of the present invention using stoichiometric amounts of the catalyst.

Without being bound to the theory, it is assumed that the electron transferring catalyst used in the present invention transfers an electron to the peroxide reagent according to the general formula (I), which results in the fragmentation of the peroxide reagent and the formation of a $(C_nF_{2n+1})$O-radical and an $(C_nF_{2n+1})$O-anion (wherein in both the radical species and the anion species, n is an integer in the range from 1 to 4). The $(C_nF_{2n+1})$O-radical presumably then reacts with the arene or heteroarene substrate by means of formal C—H substitution, which means that a C—H bond of the arene or heteroarene is formally substituted with a $(C_nF_{2n+1})$O-group, thereby providing perfluoroalkoxy-substituted arenes or heteroarenes in a (formal) radical C—H substitution reaction (wherein in these formulae n is an integer in the range from 1 to 4). The reaction is overall redox-neutral as an electron is transferred back to the catalyst in the course of the catalytic cycle.

Suitable electron transferring catalysts for use in the methods of the present invention generally include metal compounds, i.e. (transition) metal salts and transition metal coordination complexes; stable aminoxyl radical compounds, and organic dyes.

The definition of a "(transition) metal salt" for the purpose of the present invention is in accordance with the common understanding of the skilled person, i.e. a (transition) metal salt is an ionic assembly of (transition) metal cations and organic or inorganic anions, such as e.g. halides ($F^-$, $Cl^-$, $Br^-$, $I^-$), sulfate ($SO_4^{2-}$), phosphate ($PO_4^{3-}$), pentafluorosulfate ($SF_5^-$), hexafluorophosphate ($PF_6^-$), cyanide ($CN^-$), Thiocyanate ($SCN^-$). "(transition) metal salts" intends to denote the group of metal salts, comprising the more specific group of transition metal salts. The term "transition metal" intends to denote a metal selected from groups 3 to 12 of the periodic system.

While metal salts suitable for use as the electron transferring catalyst in the methods of the present invention include main group III metal salts (preferably aluminum salts, more preferably aluminum halides including, but not limited to $AlCl_3$), transition metal salts are preferred as electron transferring catalyst over main group metal salts. In this regard, it is noted that salts derived from alkali metal and earth alkali metals (such as e.g. $Na_2SO_4$, KCl, $MgCO_3$ etc.) are not suitable for use as electron transferring catalyst in the methods of the present invention.

Transitions metal salts preferably used as electron transferring catalyst in the methods of the present invention include salts from e.g. Cu, Fe, Ti, which also includes salts of the these metals at different oxidation states.

Examples for transition metal salts for use as the electron transferring catalyst in the methods of the present invention include, but are not limited to Cu(I) salts such as $Cu_2O$, CuCl, $CuCl_2$, CuBr, CuI, CuSCN; Cu(II) salts such as $CuSO_4$, $CuCO_3$; Fe(II) salts such as $FeSO_4$; Ti(III) salts such as $TiCl_3$.

The definition of a "transition metal coordination complex" for the purpose of the present invention is also in accordance with the common understanding of the skilled person, i.e. it consists of a central atom or ion (coordination center) bound by an array of molecules or ions (ligands). The transition metal coordination complex may be neutral or it may form the anionic or cationic part of a salt. Some transition metal coordination complex compounds have the ability to absorb visible light, thereby getting into an activated form suitable for electron transfer.

Transitions metal coordination complexes compounds preferably used as electron transferring catalyst in the methods of the present invention include coordination complex compounds from Cu, Ru and Ir, which also includes coordination complexes of these metals at different oxidation states.

Examples for transition metal coordination complex compounds for use as the electron transferring catalyst in the methods of the present invention include, but are not limited to Cu(I) compounds such as $Cu(MeCN)_4PF_6$; Ru(II) compounds such as $Ru(bpy)_3(PF_6)_2$ (wherein bpy=2,2'-bipyridine); Ir(III) compounds such as $[Ir(dF(CF_3)ppy)_2(dtbbpy)]PF_6$ (wherein $dF(CF_3)ppy$=2-(2,4-difluorophenyl)-5-(trifluoromethyl)pyridine; dtbbpy=4,4'-di-tert-butyl-2,2'-bipyridine) and fac-$Ir(ppy)_3$ (wherein ppy=2-phenylpyridine). $Ru(bpy)_3(PF_6)_2$ is particularly preferred as the electron transferring catalyst in the methods of the present invention.

$Ru(bpy)_3(PF_6)_2$, $Ir(ppy)_3$, $[Ir(dF(CF_3)ppy)_2(dtbbpy)]PF_6$ can be prepared according to literature procedures (D. Hanss, J. C. Freys, G. Bernandinelli, O. S. Wenger, *Eur. J. Inorg. Chem.* 2009, 4850).

Stable aminoxyl radical compounds act as redox-active agents and are therefore suitable for use as electron transferring catalyst in the methods of the present invention. Examples for such compounds that have been found to be active as an electron transferring catalyst in the methods of the present invention are the stable aminoxyl radical compound 2,2,6,6-tetramethylpiperidinyloxyl ("TEMPO") and derivatives thereof, including, but not limited to 4-hydroxy-TEMPO, i.e. 4-hydroxy-2,2,6,6-tetramethylpiperidinyloxyl ("TEMPOL").

An "organic dye" for the purpose of the present invention is an organic compound, which has the ability to absorb visible light, thereby getting into an activated form suitable for electron transfer. Examples of organic dyes useful as electron transferring catalyst in the methods of the present invention include e.g. Fluorescein, Eosin (such as e.g. Eosin Y) and 9-mesityl-10-methylacridinium perchlorate.

Depending on the electron transferring catalyst used, the methods of the present invention are carried out in the absence of light irradiation, preferably induced thermally, or photocatalytically (i.e. under light irradiation).

In the photocatalytic embodiment, an electron transferring catalyst is used, which has the capability to absorb light, thereby getting into an activated state suitable for electron transfer In that case, the electron transferring catalyst represents a “photocatalyst”.

In the other embodiment, the catalytic activity of the electron transferring catalyst does not depend on light irradiation. In this embodiment, the catalytic activity preferably is induced thermally. In these cases, the methods of the present invention are catalytic, but not photocatalytic methods. “Induced thermally” intends to denote that the reaction is performed at a temperature which is at least sufficient to induce the catalytic activity. This means that the reaction can be performed by heating the mixture to the reaction temperature, but, depending on the selected reagents and catalyst, the reaction can also proceed at room temperature or below room temperature. Although this embodiment does not depend on light irradiation, this does not intend to mean that any light source must be excluded during the methods according to this embodiment.

Due to their ability to absorb visible light, transition metal coordination complexes and organic dyes as described above are preferably used as photocatalysts in the present invention, i.e. the methods are then carried out under light irradiation in order to bring the catalyst in an activated state suitable for electron transfer. Transition metal coordination complexes are more preferred than organic dyes for use as photocatalysts in the present invention.

Transition metal coordination complexes suitable as photocatalysts in the methods of the present invention include Ru(II) compounds such as $Ru(bpy)_3(PF_6)_2$; Ir(III) compounds such as $[Ir(dF(CF_3)ppy)_2(dtbbpy)]PF_6$ and fac-$Ir(ppy)_3$; wherein $Ru(bpy)_3(PF_6)_2$ is a particularly preferred photocatalyst for use in the methods of the present invention.

The light used for activation of the photocatalyst in the photocatalytic embodiment of present invention is preferably visible light. For the purpose of the present invention, “visible light” is defined as having a wavelength λ ranging from 380 nm to 700 nm, including violet light (with λ typically being in the 10 range from 380 nm to <435 nm), blue light (with λ typically being in the range from 435 nm to <500 nm), cyan light (with λ typically being in the range from 500 nm to <520 nm), green light (with λ typically being in the range from 520 nm to <565 nm), yellow light (with λ typically being in the range from 565 nm to <590 nm), orange light (with λ typically being in the range from 590 nm to <625 nm) and red light (with λ typically being in the range from 625 nm to 700 nm). In a more preferred embodiment, the visible light is selected from the group consisting of violet light, blue light, cyan light and green light for the irradiation.

Practically, the irradiation in the methods of the present invention can be carried out using light emitting diodes covering different wavelength ranges and typically indicating a wavelength maximum ($\lambda_{max}$). For blue light irradiation, an LED with a $\lambda_{max}$ of 440 nm can for example be used.

In general, the methods of the present invention are preferably carried out photocatalytically using a transition metal coordination complex as described above, particularly $Ru(bpy)_3(PF_6)_2$, as the electron transferring catalyst (photocatalyst), or non photocatalytically, preferably thermally, using a stable aminoxyl radical compound as described above, particularly TEMPO, as the electron transferring catalyst.

Substrates suitable for use in the present invention include arene and heteroarene compounds, which are transferred into perfluoroalkoxy-substituted arenes and heteroarenes following the methods of the present invention, wherein $CF_3O$- and tert-$C_4F_9O$-substituted arenes and heteroarenes are preferred, with $CF_3O$-substituted arenes and heteroarenes being particularly preferred.

In accordance with the common understanding of the skilled person, “arenes” for the purpose of the present invention are defined as aromatic hydrocarbons, such as benzenes and naphthalenes.

In accordance with the common understanding of the skilled person, “heteroarenes” for the purpose of the present invention are aromatic hydrocarbons, wherein at least one carbon atom is replaced by a heteroatom such as nitrogen, sulfur or oxygen. Heteroarenes suitable for use in the present invention include, but are not limited to pyridines, furans, pyrroles, thiophenes, pyrazoles, imidazoles, benzimidazoles, indoles, quinolines, isoquinolines, purines, pyrimidines, thiazoles, pyrazines, oxazoles and triazoles. Pyridines are preferred heteroarenes for use in the present invention, particularly aminopyridines, halopyridines and cyanopyridines.

The arenes and heteroarenes for use in the present invention can be substituted with one or more functional groups, including, but not limited to:

- lower alkyl (i.e. C1-C6 alkyl), including linear, branched and cyclic isomers, such as e.g. methyl, ethyl, n-propyl, iso-propyl, n-butyl, iso-butyl, tert-butyl, n-pentyl, iso-pentyl, cyclo-pentyl, n-hexyl, cyclo-hexyl;
- higher alkyl (i.e. C7-C12 alkyl), including linear, branched and cyclic isomers, such as e.g. n-heptyl, cyclo-heptyl, n-octyl, cyclo-octyl, n-nonyl, n-decyl, n-dodecyl;
- halides, including F, Cl, Br, I;
- oxygen containing functional groups, including, but not limited to hydroxyl, carbonyl, aldehyde, carboxyl, carboalkoxy (e.g. carbomethoxy, carboethoxy, carbo-iso-propoxy, carbo-tert-butoxy), alkoxy (e.g. methoxy, ethoxy, iso-propoxy, tert-butoxy), silyloxy;
- nitrogen containing functional groups, including but not limited to amide, amine, nitrile, nitro;
- sulfur containing functional groups, including but not limited to: thiol, thioether, sulfoxide, sulfone, thiocyanate;
- boron containing functional groups, including but not limited to boronic acids, boronic acid esters.

The arenes and heteroarenes for use in the present invention as well as the functional groups described above can in principle also be substituted with one or more aromatic and heteroaromatic functional groups including, but not limited to phenyl, benzyl, pyridinyl, furanyl, pyrrolyl, thiophenyl, pyrazolyl, imidazolyl, benzimidazolyl, indolyl, quinolinyl, isoquinolinyl, purinyl, pyrimidinyl, thiazolyl, pyrazinyl, oxazolyl and triazolyl. However, in that case, it needs to be kept in mind that such groups may also react with the peroxide reagent in the methods of the present invention. Therefore, it is preferred in the present invention that the arene and heteroarenes used as substrates in the methods of the present invention are not substituted with aromatic and heteroaromatic functional groups, or with functional groups that contain aromatic or heteroaromatic moieties. Similar considerations apply to functional groups that contain olefin or acetylene moieties.

Preferred arenes for use in the methods of the present invention include, but are not limited to benzene and derivatives thereof, fluorobenzene and derivatives thereof; chlorobenzene and derivatives thereof; bromobenzene and derivatives thereof; benzonitrile and derivatives thereof; benzaldehyde and derivatives thereof; benzoic acid and derivatives thereof; benzoic acid ester (such as e.g. benzoic acid methyl ester) and derivatives thereof; benzamide and derivatives thereof; phenyl boronic acid and derivatives thereof; wherein "derivatives thereof" means that one or more further functional groups as described above can be present in the arene compound.

(Hetero)arenes are preferred substrates in the photocatalytic embodiment of the present invention, especially if a transition metal coordination complex, such as $Ru(bpy)_3(PF_6)_2$, is used as the electron transferring catalyst (photocatalyst); and/or $(OCF_3)_2$ is used as the peroxide reagent.

Preferred heteroarenes for use in the methods of the present invention are pyridines, especially if a stable aminoxyl radical compound, preferably TEMPO, is used as the electron transferring catalyst; and/or $(OCF_3)_2$ is used as the peroxide reagent.

Trifluoromethoxylated pyridines are highly attractive building blocks in pharmaceutical and agricultural chemistry, but access to trifluoromethoxylated pyridine building blocks is limited due to synthetic challenges. It has been found herein that the methods of the present invention, in particular those wherein TEMPO is used as the electron transferring catalyst, are particularly suitable in order to provide perfluoroalkoxylated, in particular trifluoromethoxylated pyridines in one step.

One advantage of using the methods of the present invention in the preparation of perfluoroalkoxylated, in particular trifluoromethoxylated pyridines, is that the electron deficient 4-position of the pyridine substrate is typically not substituted due to the electrophilic nature of the $(C_nF_{2n+1})$O-radical (wherein in this formula, n is an integer in the range from 1 to 4) formed in the fragmentation of the peroxide reagent according to formula (I). This facilitates the separation of possible regioisomers.

Preferred pyridine substrates for use in the present invention, particularly if TEMPO is used as the electron transferring catalyst and/or $(OCF_3)_2$ is used as the peroxide reagent, include, but are not limited to halopyridines, in particular 2-halopyridins (wherein "halo" means fluoro, chloro and bromo, preferably chloro and bromo), aminopyridines and cyanopyridines. Examples include, but are not limited to 2-bromopyridine, 2-bromo-6-methylpyridine, 2-chloropyridine, 2-fluoro-6-aminopyridine, 2-bromo-4-fluoropyridine, 2-cyanopyridine, 3-cyanopyridine, 4-cyanopyridine, 2-fluoro-6-cyanopyridine, 2-fluoro-5-cyanopyridine, 2-amino-6-fluoropyridine, 2-amino-6-chloropyridine with 2-amino-6-chloropyridine and 2-cyanopyridine being particularly preferred. The perfluoroalkoxy-substituted pyridines, in particular the trifluoromethoxy-substituted pyridines resulting from these substrates all represent excellent building blocks, which are accessible in only one single step by means of the methods of the present invention.

In relation to the peroxide reagent, the (hetero)arene substrate is typically used in excess molar amounts in the methods of the present invention. Typical molar ratios of peroxide reagent according to formula (I) and (hetero)arene substrate in the methods of the present invention include 1:2, 1:3, 1:4, 1:5, 1:6, 1:7, 1:8, 1:9, 1:10, 1:11, 1:12, 1:13, 1:14 and 1:15.

Using excess molar amounts of the arene or heteroarene substrates in relation to the peroxide has the advantage that the yield is improved and over-substitution is strongly diminished. The ratio of peroxide reagent according to formula (I) and the arene or heteroarene substrate is thus a compromise between efficacy of the reaction and economical/ecological aspects. Taking this into consideration, it is preferred that the peroxide reagent and the arene or heteroarene substrate are used in molar ratios of 1:5, 1:6, 1:7, 1:8, 1:9, 1:10, 1:11 or 1:12, 1:13, 1:14, 1:15 with molar ratios of 1:5, 1:6, 1:7, 1:8 and 1:10 being more preferred. Multiple substitution products are typically only observed in trace amounts if at least 5 equivalents of (hetero)arene substrate is used in relation to the peroxide reagent. In any event, multiple substitution products can be separated from the mono-substituted product(s) by means of purification techniques known to the skilled person, such as chromatographic methods (e.g. column chromatography or HPLC) and distillation methods (including distillations on an industrial scale).

The methods of the present invention can be performed in the presence of an organic solvent. However, they can also be performed "neat", i.e. in the absence of solvent, in particular if the arene or heteroarene substrate is a liquid at the reaction temperature, for example room temperature.

In general, high concentrations of the arene or heteroarene substrate in the reaction mixture are favorable in terms of improving the yield of the substitution reaction according to the methods of the present invention. At some point, however, a very high substrate concentration may result in practical problems regarding the distribution of chemicals in the mixture, in particular if the substrate is a solid compound at the reaction temperature, for example room temperature. The reaction mixture may then become a very thick slurry, which leads to a non-ideal distribution of components, thereby reducing yield of the reaction and should therefore be avoided. If that is the case, use of an organic solvent is preferable.

An organic solvent in some cases may also be useful if the catalyst is not soluble in the (liquid) arene or heteroarene substrate.

If an organic solvent is used in the methods of the present invention, the concentration of the arene or heteroarene in the solvent is typically within the range of 0.1 mol/L to 10 mol/L, preferably 0.2 mol/L to 8 mol/L, more preferably 0.5 mol/L to 6 mol/L, even more preferably 1 mol/L to 5 mol/L, including concentrations of e.g. 1.5 mol/L, 2 mol/L, 2.5 mol/L, 3 mol/L, 3.5 mol/L, 4 and 4.5 mol/L.

Suitable organic solvents for use in the present invention are typically polar aprotic solvents including, but not limited to acetonitrile (MeCN), acetone, N,N-dimethylformamide (DMF), dimethylsulfoxide (DMSO), tetrahydrofuran (THF), diethylether, iso-propylether (IPE), methyl-tert-butylether (MTBE), 1,4-dioxane, ethyl acetate (EtOAc), dichloromethane (DCM), 1,2-dichloroethane (1,2-DCE), chloroform and mixtures thereof. Acetonitrile, acetone and dichloromethane are preferred solvents for use in the present invention, acetonitrile is particularly preferred. Where appropriate, mixtures of two or more solvents can be used for the methods according to the present invention.

The methods of the present invention can optionally be carried out in the presence of an additive, which is typically a salt additive, in particular an alkali or earth alkali metal salt additive. It is believed that the additive helps to regenerate TEMPO and enables a catalytic process. Where appropriate, mixtures of two or more additives can be used for the methods according to the present invention.

Suitable additives for use in the methods of the present invention include, but are not limited to alkali and earth alkali metal carbonates and hydrogen carbonates, such as e.g. $Li_2CO_3$, $Na_2CO_3$, $K_2CO_3$, $MgCO_3$, $CaCO_3$, $LiHCO_3$, $NaHCO_3$, $KHCO_3$; alkali and earth alkali metal sulfates, such as e.g. $Li_2SO_4$, $Na_2SO_4$, $K_2SO_4$, $MgSO_4$, $CaSO_4$; alkali and earth alkali metal phosphates, hydrogen phosphates and dihydrogen phosphates, such as e.g. $Li_3PO_4$, $Li_2HPO_4$, $LiH_2PO4$, $Na_3PO_4$, $Na_2HPO_4$, $NaH_2PO_4$, $K_3PO_4$, $K_2HPO_4$, $KH_2PO_4$, $CaHPO_4$; alkali and earth alkali metal halides such as e.g. LiF, NaF, KF, CsF, $MgF_2$, $CaF_2$, LiCl, NaCl, KCl, CsCl, $MgCl_2$, $CaCl_2$, LiBr, NaBr, KBr, Csbr, $MgBr_2$, $CaBr_2$, LiI, NaI, KI, CsI, $MgI_2$, and $CaI_2$; Alkali and earth alkali metal carbonates and fluorides are preferred additives for use in the methods of the present invention, in particular $Na_2CO_3$, $K_2CO_3$ and KF.

Typical amounts of catalysts used in the method of the present invention are within the range of 0.01 to 2 equivalents, preferably 0.05 to 1 equivalent, more preferably 0.1 to 0.5 equivalent, based on the molar amount of the peroxide reagent according to the general formula (I).

Catalyst loadings described herein generally refer to the molar amount of reactant that is present in lower molar amounts in the reaction mixture in relation to the other reactant. “Reactants” in the methods of the present invention mean the arene/heteroarene substrate on the one hand, and the peroxide reagent according to the general formula (I) on the other hand. Since the arene/heteroarene is typically used in molar excess amounts with respect to the peroxide reagent according to the general formula (I), catalyst loadings referred to herein are typically in relation to the molar amount of the peroxide reagent unless otherwise indicated. If for example 1 equivalent (or 100 mol-%) of the peroxide reagent is used, a catalyst loading of e.g. 10 mol-% is in relation to the molar amount of peroxide reagent.

The methods of the present invention can in principle be performed with high catalyst loadings of up to 1 equivalent (100 mol-%). In that case, the electron transferring catalyst may be considered as “mediating” the formal C—H substitution reaction of the present invention. For example, it has been found by the inventors that copper compounds, such as e.g. CuCl and $Cu(MeCN)_4PF_6$, are particularly useful as electron transferring catalyst at stoichiometric amounts in the methods of the present invention.

However, it is of course preferred that the electron transferring catalyst of the present invention is used as a “real catalyst” at substoichiometric amounts. Substoichiometric amounts of the electron transferring catalyst useful in the present invention include for example 50 mol-% and below, 40 mol-% and below, and 30 mol-% and below.

This includes amounts within the range of 0.01 mol-% to 30 mol-%, preferably within the range of 0.05 mol-% and 25 mol-%, more preferably within the range of 0.1 mol-% and 20 mol-%, even more preferably within the range of 0.5 mol-% and 18 mol-%, even more preferably within the range of 1 mol-% and 16 mol-%, even more preferably within the range of 1 mol-% and 14 mol-%, even more preferably within the range of 1 mol-% and 12 mol-%, even more preferably within the range of 1 mol-% and 10 mol-%, even more preferably within the range of 1 mol-% and 8 mol-%, including catalyst loadings of e.g. 1.5 mol-%, 2 mol-%, 2.5 mol-%, 3 mol-%, 3.5 mol-%, 4 mol-%, and 4.5 mol-%, 5.0 mol-%, 5.5 mol-%, 6.0 mol-%, 6.5 mol-%, and 7.5 mol-%.

Of course, the catalyst loading also depends on the particular catalyst used.

If for example a (transition) metal salt is used as the electron transferring catalyst in the methods of the present invention, catalyst loadings, as mentioned above, can be up to 1 eq. Preferably, however, catalyst loadings with transition metal salts are within the range of 5 mol-% to 50 mol %, more preferably within the range of 7.5 mol-% and 40 mol-%, even more preferably within the range of 10 mol-% and 30 mol-%.

Using a transition metal coordination complex as the electron transferring catalyst often allows lower catalyst loadings. Hence, with such compounds, the methods of the present invention are preferably carried out photocatalytically under visible light irradiation.

If a transition metal coordination complex, such as the particularly preferred $Ru(bpy)_3(PF_6)_2$, is used as the electron transferring catalyst in the methods of the present invention, catalyst loadings are preferably within range from 0.1 mol-% and 6 mol-%, including catalyst loadings of e.g. 0.25 mol-%, 0.5 mol-%, 0.75 mol-%, 1 mol-%, 1.25 mol-%, 1.5 mol-%, 1.75 mol-%, 2 mol-%, 2.25 mol-%, 2.5 mol-%, 2.75 mol-%, 3 mol-%, 3.25 mol-%, 3.5 mol-%, 3.75 mol-%, 4 mol-%, 4.25 mol-%, 4.5 mol-%, 4.75 mol-%, 5 mol-%, 5.25 mol-%, 5.5 mol-%, and 5.75 mol-%.

Catalyst loadings in the range of 1 mol-% and 4 mol-% are particularly preferred for $Ru(bpy)_3(PF_6)_2$ as the electron transferring catalyst. The methods of the present invention are then preferably carried out photocatalytically, i.e. under light irradiation, wherein the light is visible light, preferably selected from violet light, blue light, cyan light and green light; and/or with bis-trifluoromethylperoxide ($(OCF_3)_2$) as the peroxide reagent according to the general formulae (I); and/or with arene or pyridine substrates, optionally substituted with one or more functional groups as described above, wherein the pyridine substrates are preferably selected from the group consisting of aminopyridines, cyanopyridines and halopyridines.

If a stable aminoxyl radical compound, such as the particularly preferred TEMPO, is used as the electron transferring catalyst in the methods of the present invention, catalyst loadings are preferably within the range from 5 mol-% and 30 mol-%, including catalyst loadings of e.g. 7.5 mol-%, 10 mol-%, 12.5 mol-%, 15 mol-%, 17.5 mol-%, 20 mol-%, 22.5 mol-%, 25 mol-%, and 27.5 mol-%. In that case, the methods are preferably carried out with bis-trifluoromethylperoxide ($(OCF_3)_2$) as the peroxide reagent according to the general formulae (I); and/or with pyridine substrates, optionally substituted with one or more functional groups as described above, in particular with pyridine substrates selected from the group consisting of aminopyridines, cyanopyridines and halopyridines.

The methods according to the present invention can be carried out at a temperature which is suitably selected according to e.g. reactivity of the reagents, the catalysts, the solvents and/or the regioselectivity of the method. This includes temperatures within the range of 0° C. to 80° C., preferably within the range of 10° C. and 50° C., and more preferably within the range of 20° C. and 30° C.

In an alternative embodiment of the present invention, the electron transferring catalyst can also be replaced by an electric current, for example, if the C—H substitution or direct perfluoroalkoxylation of an arene or heteroarene with a $(C_nF_{2n+1})$O-group (wherein in this formula, n is an integer in the range from 1 to 4) using a peroxide reagent according to the general formula (I) is carried out in an electrode-electrode interface. In that case, the peroxide reagent according to the general formula (I) is electrochemically fragmented under $(C_nF_{2n+1})$O-radical formation, e.g. by means of contacting the negatively charged electrode in an electrode-electrode interface, and said $(C_nF_{2n+1})$O-radical then substitutes a C—H bond of an arene or heteroarene with a ($C_nF_{2n+1}$)O-group (wherein in the above formulae, n is an integer in the range from 1 to 4).

The advantage of this electrochemical alternative method of the present invention is that reagent waste is reduced, thereby providing a more economical and ecological version of the methods of the present invention.

The following examples are intended to illustrate the present invention without limiting its scope. Should the disclosure of any patents, patent applications, and publications which are incorporated herein by reference conflict with the description of the present application to the extent that it may render a term unclear, the present description shall take precedence.

EXAMPLES

General

The reactions according to the following examples with a maximum scale of 1 mmol were conducted in pressure tubes "P26 0001", larger scales were conducted in pressure tubes "P26 0006" from FengTecEx GmbH. Dry Solvents were prepared by filtering purchased HPLC- or analytical grade solvents through Aluminium oxide and storing them over activated Molecular sieves (3 or 4 Å) for at least two days. The experiments were all conducted under argon, dry working techniques and/or degassed and/or dry solvents if stated. Blue light irradiation was provided by LED strips ($\lambda_{max}$=440 nm, IP65) purchased from PB Versand GmbH (Type: 5630). A crystallization flask wrapped with the LED strips was used as a light reactor.

NMR spectra were acquired on a JEOL ECX 400 (400 MHz), JEOL ECP 500/Bruker Avance 500 (500 MHz), Varian INOVA 600 (600 MHz) or a Bruker Avance 700 (700 MHZ) in $CDCl_3$, $CD_3CN$ or ($(CD_3)_2CO$) as a solvent.

Example 1: Photocatalytic Trifluoromethoxylation of Exemplary (Hetero)Arenes A pressure tube was charged with a stir bar, $Ru(bpy)_3(PF_6)_2$ (1.5 mol %, 0.0075 mmol, 6.5 mg), MeCN (2.5 mL) and the (hetero)arene substrate (5 eq). The mixture was frozen with liquid $N_2$ and the tube was evacuated. Afterwards $(CF_3O)_2$ (1 eq, 0.5 mmol) was condensed into the tube and the tube was vented shortly with argon. The closed tube was gently shaken in water until the mixture melted and was stirred for 16 h at room temperature under irradiation from blue LEDs. Afterwards, the tube was carefully opened towards the rear side of the fume hood to release overpressure. The internal standard trifluorotoluene (1 eq, 61 μL) was added and the mixture was vigorously shaken. Up to 1 mL of the reaction mixture was filtered through diatomaceous earth and transferred into an NMR-tube for $^{19}$F-NMR-Analysis.

The product yields according to the following Table 1 were calculated from the $^{19}$F-NMR Spectrum using trifluorotoluene as an internal standard.

TABLE 1

| Entry | Arene 1a | Product ($^{19}$F NMR yield) | Regioselectivity (ortho-/meta-/para) |
|---|---|---|---|
| 1 | Benzene | 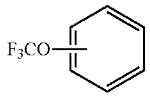<br>74%[a]<br>(64%) | — |
| 2 | Fluoro-benzene | 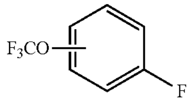<br>58%[a]<br>58% | 2.5/1/2.3[a]<br>2.1/1/1.8 |
| 3 | Chloro-benzene | 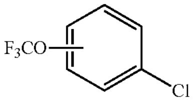<br>49% | 1.8/1/1.3 |
| 4 | Bromo-benzene | 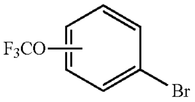<br>60%[a] | 2.9/1/2.1[a] |
| 5 | Benzo-nitrile | 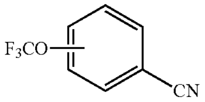<br>69%[a] | 2.3/1.6/1[a] |
| 6 | Benzalde-hyde | 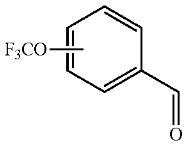<br>60%[a]<br>63% | 2.1/1.9/1[a]<br>2.4/2.4/1 |
| 7 | Benzoic acid | 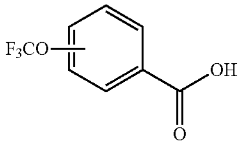<br>49%[a] | 1.9/2.1[a] |
| 8 | Benzoic acid methyl ester | 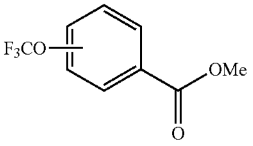<br>73%[a] | 1.8/2.1/1[a] |

TABLE 1-continued

| Entry | Arene 1a | Product ($^{19}F$ NMR yield) | Regioselectivity (ortho-/meta-/para) |
|---|---|---|---|
| 9 | Aceto-phenone | 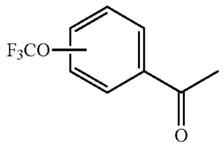 70%[a] 75% | 1.7/1.7/1[a] 1.9/1.9/1 |
| 10 | Phenyl-boronic acid pinacol ester | 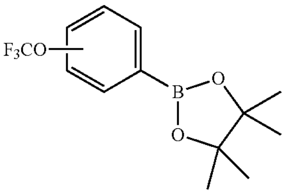 | 1.6/1.4/1 |
| 11 | Nitro-benzene | 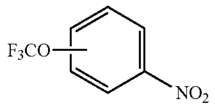 54%[a] | 1/4.2/1.5[a] |
| 12 | 2-amino-6-chloro-pyridine[b] | 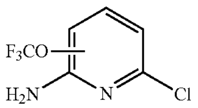 37% | n.d. |

[a]with 0.1 equiv KF
[b]increased scale based on 3 mmol of $(OCF_3)_2$

Table 1 illustrates that trifluoromethoxy-substituted (hetero)arenes with a broad substrate scope can be obtained in moderate to good yields (37-75%) using the (photocatalytic) method of the present invention for their preparation.

Example 2: TEMPO-Catalyzed Trifluoromethoxylation of Exemplary Arenes and Pyridines A pressure tube was charged with a stir bar, TEMPO (5 mol %, 0.025 mmol, 3.9 mg), $K_2CO_3$ (1 eq, 0.5 mmol, 69.1 mg) and the (hetero)arene substrate (5 eq). The mixture was frozen with liquid $N_2$ and the tube was evacuated. Afterwards, $(CF_3O)_2$ (1 eq, 0.5 mmol) was condensed into the tube and the tube was vented shortly with argon. The closed tube was gently shaken in water until the mixture melted and was stirred for 16 h at room temperature. Afterwards, the tube was carefully opened towards the rear side of the fume hood to release overpressure, the internal standard trifluorotoluene (1 eq, 61 μL) and MeCN (to achieve 0.2 M) was added and the mixture was vigorously shaken. Up to 1 mL of the reaction mixture was filtered through diatomaceous earth and transferred into an NMR-tube for $^{19}F$-NMR-Analysis.

The product yields according to the following Table 2 were calculated from the $^{19}F$-NMR Spectrum using trifluorotoluene as an internal standard.

TABLE 2

| Entry | Arene 2a | Product ($^{19}F$ NMR yield) | Regio-selectivity (ortho-/meta-/para) |
|---|---|---|---|
| 1 | Benzene | 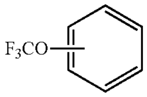 61% | — |
| 2 | Benzonitrile[a] | 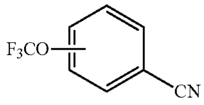 81% | 1.4/1.6/1 |
| 3 | Benzoic acid methyl ester | 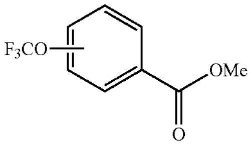 45% | 1/1.9/1.2 |
| 4 | 2-Chloropyridine | 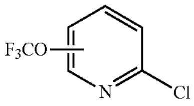 12% | n.d. |

[a]10 equivalents of arene were used

Table 2 illustrates that trifluoromethoxy-substituted arenes can be obtained in moderate to very good yields (Table 2, entries 1-3: 45-81%) using the (TEMPO-catalyzed) method of the present invention for their preparation.

Table 2 also shows that under the chosen conditions, trifluoromethoxylation of 2-chloropyridine in principle occurs (Table 2, entry 4: 12%). This encouraging result led the inventors to the development of improved conditions for the trifluoromethylation of 2-halopyridines, which are important building blocks.

Example 3: Improved Conditions for the TEMPO-Catalyzed Trifluoromethoxylation of Exemplary Pyridines A pressure tube was charged with a stir bar, TEMPO (25 mol %, 0.125 mmol, 19.5 mg), $Na_2CO_3$ (1 eq, 0.5 mmol, 53 mg) and the pyridine substrate (5 eq). The mixture was frozen with liquid $N_2$ and the tube was evacuated. Afterwards $(CF_3O)_2$ (1 eq, 0.5 mmol) was condensed into the tube and the tube was vented shortly with argon. The closed tube was gently shaken in water until the mixture melted and was stirred 16 h at room temperature. Afterwards the tube was carefully opened towards the rear side of the fume hood to release overpressure. The internal standard trifluorotoluene (1 eq, 61 μL) and MeCN or $Et_2O$ (to achieve 0.2 M) was added and the mixture was vigorously shaken. Up to 1 mL of the reaction mixture was filtered through diatomaceous earth and transferred into an NMR-tube for $^{19}F$-NMR-Analysis.

The product yields according to the following Table 3 were calculated from the $^{19}F$-NMR Spectrum using trifluorotoluene as an internal standard.

TABLE 3

| Entry | Pyridine 3a | Product ($^{19}F$ NMR yield) | Regioselectivity |
|---|---|---|---|
| 1 | 2-Bromopyridine[a] | 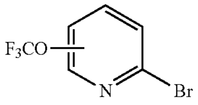 43% | n.d. |
| 2 | 2-Bromo-6-methylpyridin | 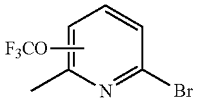 47% | n.d. |
| 3 | 2-chloropyridin[b] | 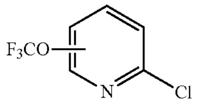 51% | n.d. |
| 4 | 2-Bromo-4-fluoropyridine | 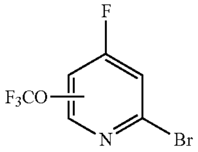 66% | n.d. |
| 5 | 2-Cyanopyridine[b] | 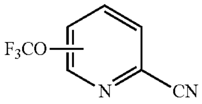 31% | n.d. |
| 6 | 3-Cyanopyridine[c] | 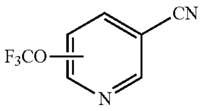 31% | n.d. |
| 7 | 4-Cyanopyridine[d] | 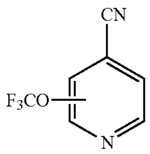 29% | n.d. |
| 8 | 2-amino-6-fluoropyridine[e] | 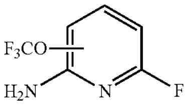 39% | n.d. |

TABLE 3-continued

| Entry | Pyridine 3a | Product ($^{19}F$ NMR yield) | Regioselectivity |
|---|---|---|---|
| 9 | 2-amino-6-chloropyridine[e] | 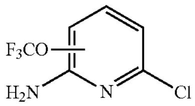 27% | n.d. |

[a]10 mol % TEMP, 65° C.
[b]increased scale based on 6 mmol of $(OCF_3)_2$
[c]increased scale based on 6 mmol of $(OCF_3)_2$ in 3 ml MeCN
[d]increased scale based on 6 mmol of $(OCF_3)_2$ in 30 ml MeCN
[e]2.5 ml MeCN Table 3 illustrates that trifluoromethoxy-substituted 2-halopyridines can be obtained in moderate to good yields (Table 3, entries 1-4: 43-66%) using the (TEMPO-catalyzed) method of the present invention for their preparation.

Table 3 furthermore shows that trifluoromethoxy-substituted cyanopyridines (Table 3, entries 5-7) as well as the trifluoromethoxy-substituted 2-amino-6-fluoropyridine and 2-amino-6-chloropyridine (Table 3, entry 8-9) are also obtained following the (TEMPO-catalyzed) method of the present invention for their preparation, although with slightly lower yield (27-39%). Most importantly, only one reaction step is required in order to access those otherwise difficult to synthesize perfluoroalkoxylated pyridines that have the potential to serve as excellent building blocks.

Example 4: CuCl-Mediated Trifluoromethoxylation of Benzene

The pressure tube was charged with a stir bar, CuCl (1 eq, 0.5 mmol, 49.5 mg), MeCN (0.25 mL) and benzene (5 eq). The mixture was frozen with liquid $N_2$ and the tube was evacuated. Afterwards $(CF_3O)_2$ (1 eq, 0.5 mmol) was condensed into the tube and the tube was vented shortly with argon. The closed tube was gently shaken in water until the mixture melted and was stirred 16 h at room temperature. Afterwards the tube was carefully opened towards the rear side of the fume hood to release overpressure, because carbonyl fluoride is formed as a side product during the reaction. The internal standard trifluorotoluene (1 eq, 61 μL) and MeCN (to achieve 0.2 M) was added and the mixture was vigorously shaken. Up to 1 mL of the reaction mixture was filtered through diatomaceous earth and transferred into an NMR-tube for $^{19}F$-NMR-Analysis.

The product trifluoromethoxy benzene was obtained with 55% yield (calculated from the $^{19}F$-NMR Spectrum using trifluorotoluene as an internal standard).

Taking into consideration that perfluoroalkoxylated, in particular trifluoromethoxylated arenes and heteroarenes, including trifluoromethoxylated pyridines as a highly useful class of building blocks, are generally difficult to access, Examples 1-4 provided herein illustrate that the methods of the present invention serve as a valuable tool for the provision of such compounds with moderate to very good yields, thereby broadening the scope for the direct perfluoroalkoxylation of arene and heteroarene substrates.

The invention claimed is:

1. A method for the preparation of $(C_nF_{2n+1})$O-substituted arenes and heteroarenes characterized in that a peroxide reagent according to the following general formula (I)

$$(OC_nF_{2n+1})_2 \qquad (I),$$

is fragmented in the presence of an electron transferring catalyst under $(C_nF_{2n+1})$O-radical formation, and said $(C_nF_{2n+1})$O-radical then substitutes a C—H bond of an arene or heteroarene with a $(C_nF_{2n+1})$O-group, wherein in the above formulae n is an integer in the range from 1 to 4.

2. A method for the direct perfluoroalkoxylation of arenes and heteroarenes with a $(C_nF_{2n+1})$O-group, characterized in that a peroxide reagent according to the following general formula (I)

$$(OC_nF_{2n+1})_2 \qquad (I),$$

is fragmented in the presence of an electron transferring catalyst under $(C_nF_{2n+1})$O-radical formation, and said $(C_nF_{2n+1})$O-radical then substitutes a C—H bond of an arene or heteroarene with a $(C_nF_{2n+1})$O-group, wherein in the above formulae n is an integer in the range from 1 to 4.

3. The method according to claim 1, wherein n is 1 or 4.

4. The method according to claim 1, wherein the heteroarene is a pyridine.

5. The method according to claim 1, wherein the electron transferring catalyst is a metal salt.

6. The method according to claim 1, wherein the electron transferring catalyst is a stable aminoxyl radical compound.

7. The method according to claim 1, wherein the method does not depend on light irradiation.

8. The method according to claim 1, wherein the electron transferring catalyst is a transition metal coordination complex.

9. The method according to claim 8, wherein the electron transferring catalyst is a photocatalyst and the method is carried out under light irradiation, wherein the light is visible light having a wavelength λ in the range from 380 nm to 700 nm.

10. The method according to claim 1, wherein the electron transferring catalyst is selected from the group consisting of $Ru(bpy)_3(PF_6)_2$, $[Ir(dF(CF_3)ppy)_2(dtbbpy)]PF_6$ and $Ir(ppy)_3$.

11. The method according to claim 1, wherein the electron transferring catalyst is present in substoichiometric amounts.

12. The method according to claim 1, wherein the arene or heteroarene is present in excess molar amounts in relation to the peroxide reagent according to the general formula (I).

13. The method according to claim 1, wherein the method is carried out in the presence of an organic solvent, wherein the solvent is a polar aprotic solvent selected from the group consisting of acetonitrile (MeCN), acetone, N,N-dimethylformamide (DMF), dimethylsulfoxide (DMSO), tetrahydrofuran (THF), diethylether, iso-propylether (IPE), methyl-tert-butylether (MTBE), 1,4-dioxane, ethylacetate (EtOAc), dichloromethane (DCM), 1,2-dichloroethane (1,2-DCE), chloroform and mixtures thereof; or in the absence of a solvent.

14. The method according to claim 1, wherein the method is carried out in the presence of an additive, wherein the additive is a salt additive selected from the group consisting of alkali and earth alkali metal sulfates, alkali and earth alkali metal carbonates and hydrogen carbonates, alkali and earth alkali metal phosphates, hydrogen phosphates, and dihydrogen phosphates, and alkali and earth alkali metal halides.

15. A method for the preparation of pharmaceutical or agrochemical compounds or building blocks for the synthesis of pharmaceutical and agrochemical compounds, comprising the method according to claim 1.

16. The method according to claim 5, wherein the electron transferring catalyst is a transition metal salt of Cu, Fe, or Ti, or wherein the electron transferring catalyst is a transition metal salt selected from the group consisting of $Cu_2O$, CuCl, $CuCl_2$, CuBr, CuI, CuSCN, $CuSO_4$, $CuCO_3$, $FeSO_4$, and $TiCl_3$.

17. The method according to claim 6, wherein the electron transferring catalyst is a stable aminoxyl radical compound selected from the group consisting of 2,2,6,6-tetramethylpiperidinyloxyl ("TEMPO") and derivatives thereof.

18. The method according to claim 8, wherein the electron transferring catalyst is a transition metal coordination complex of Cu, Ru or Ir.

19. The method according to claim 18, wherein the electron transferring catalyst is a transition metal coordination complex selected from the group consisting of $Cu(MeCN)_4PF_6$, $Ru(bpy)_3(PF_6)_2$, $[Ir(dF(CF_3)ppy)_2(dtbbpy)]PF_6$ and $Ir(ppy)_3$.

20. The method according to claim 1, wherein the electron transferring catalyst is selected from the group consisting of a metal salt, an aminoxyl radical compound, a transition metal coordination complex, an organic dye, and combinations thereof.

* * * * *